US012788839B2

(12) United States Patent
Long

(10) Patent No.: US 12,788,839 B2
(45) Date of Patent: Nov. 10, 2026

(54) HEATING CUP COMPONENT FOR ELECTRIC HEATING INCENSE BURNER

(71) Applicant: SHENZHEN SHENHONG ELECTRONICS CO., LTD., Shenzhen (CN)

(72) Inventor: Haihua Long, Shenzhen (CN)

(73) Assignee: SHENZHEN SHENHONG ELECTRONICS CO., LTD., Shenzhen (CN)

( * ) Notice: Subject to any disclaimer, the term of this patent is extended or adjusted under 35 U.S.C. 154(b) by 270 days.

(21) Appl. No.: 18/665,328

(22) Filed: May 15, 2024

(65) Prior Publication Data

US 2025/0235572 A1 Jul. 24, 2025

(30) Foreign Application Priority Data

Jan. 24, 2024 (CN) ......................... 202420178439.2

(51) Int. Cl.
*A61L 9/03* (2006.01)
*H05B 3/24* (2006.01)

(52) U.S. Cl.
CPC .................. *A61L 9/03* (2013.01); *H05B 3/24* (2013.01); *H05B 2203/002* (2013.01)

(58) Field of Classification Search
CPC ...... H05B 3/06; H05B 3/18; H05B 2203/014; H05B 2203/02; A61L 9/02; A61L 9/03; A61L 2209/135; Y10S 261/89
See application file for complete search history.

(56) References Cited

U.S. PATENT DOCUMENTS

| | | | | |
|---|---|---|---|---|
| 10,207,018 | B2 * | 2/2019 | Gasper | A61L 9/012 |
| 11,576,515 | B2 * | 2/2023 | Walker | A47J 36/26 |
| 2003/0108461 | A1 * | 6/2003 | Lo | A61L 9/03<br>422/305 |
| 2019/0022267 | A1 * | 1/2019 | Hsiao | A61L 9/03 |
| 2021/0401050 | A1 * | 12/2021 | Liu | A24F 40/57 |
| 2022/0378969 | A1 * | 12/2022 | Al Saeed | B01F 23/215 |

OTHER PUBLICATIONS

Dihong, "Thermal Insulation Cotton Expained: How It Retains Heat", webpage published Oct. 30, 2025 (Year: 2025).*

* cited by examiner

*Primary Examiner* — Jennifer Wecker
*Assistant Examiner* — Brady C Pilsbury
(74) *Attorney, Agent, or Firm* — JEEN IP LAW, LLC

(57) ABSTRACT

A heating cup component for an electric heating incense burner is provided, which includes a shell, a control board, a metal cup, an insulation sheet, an electric heating wire, and a thermal insulation cotton. The metal cup is provided in the shell, the electric heating wire is provided below the metal cup, the insulation sheet is provided on an upper surface of the electric heating wire, the control board is provided at a bottom of the shell, and the thermal insulation cotton is provided between the metal cup and the control board. The heating cup component for electric heating incense burner in the present disclosure heats more quickly and evenly, which is beneficial for improving heating efficiency and reducing energy consumption; and it is easy to clean and suitable for battery power supply, thereby improving portability and use range.

3 Claims, 3 Drawing Sheets

HEATING CUP COMPONENT FOR ELECTRIC HEATING INCENSE BURNER

CROSS-REFERENCE TO RELATED APPLICATIONS

This application claims priority to Chinese Patent Application No. 202420178439.2, filed on Jan. 24, 2024, which is hereby incorporated by reference in its entirety.

TECHNICAL FIELD

The present disclosure relates to the field of incense burner technologies, and in particular, to a heating cup component for an electric heating incense burner.

BACKGROUND

Heating cup component for electric heating incense burner generates fragrance by heating or burning incenses, and it mainly through the following heating combinations.

(1) A combination heating of a ceramic cup and heating wire, the heating wire is placed at a bottom of an inner side of the ceramic cup, and through the principle of resistance heating, the heating wire directly heats and burns the incenses. The advantage is that it has a high thermal efficiency, and the heating wire can render the temperature to be above 240 degrees, the incenses is quickly heated and burned. The disadvantage is that it cannot accurately control the heating temperature of the incenses; and under a high temperature, residual sesame oil and ash are easily generated and they are difficult to clean, thereby affecting aesthetics and user experience; which is not suitable for liquid essential oils.

(2) A combination heating of a incense cup (metal or ceramic material) with ceramic heating plate: the ceramic heating plate is placed at the bottom of the inner side of the incense cup, and the incenses are heated through the ceramic heating plate. The advantage is that precise temperature control can be achieved, and the heating temperature can be adjusted as needed to heat the incenses. The disadvantage is that the residual sesame oil after heating the incenses can affect the lifespan and appearance of the ceramic heating plate, and it needs to be used in combination with the incense plate. The incenses are placed on the ceramic heating plate and heated, thereby reducing a thermal efficiency.

(3) A heating of a metal heating plate technology: a heating plate is formed by a metal structure combined with a heating tube. The advantages are stable structure, long service life, and the ability to withstand high power. The disadvantage is that it has a large volume, capacity, and heat dissipation area, which requires high power support and is not suitable for battery power supply.

(4) A combination technology of a ceramic cup and a heating plate: the heating component is placed on a bottom of an outer side of the ceramic cup and heat the incense through conduction. The advantage is that it is easy to clean, heating more evenly, and does not require a incense plate. The disadvantage is that it cannot reach high temperatures, there is a risk of ceramic fracture, low heating efficiency, and is not suitable for battery power supply.

SUMMARY

The present disclosure provides a heating cup component for an electric heating incense burner to solve at least one of the above-mentioned technical problems.

To solve the above problems, as an aspect of the present disclosure, a heating cup component for an electric heating incense burner is provided, including a shell, a control board, a metal cup, an insulation sheet, an electric heating wire, and a thermal insulation cotton; the metal cup is provided in the shell, the electric heating wire is provided below the metal cup, the insulation sheet is provided on an upper surface of the electric heating wire, the control board is provided at a bottom of the shell, and the thermal insulation cotton is provided between the metal cup and the control board.

In an embodiment, a bottom of the metal cup includes an upward protrusion part, and the electric heating wire is located in an accommodating chamber formed by the protrusion part.

In an embodiment, the thermal insulation cotton includes a circular thermal insulation cotton and a cylindrical thermal insulation cotton, the circular thermal insulation cotton is sleeved on an outside of the cylindrical thermal insulation cotton, the electric heating wire is provided on the cylindrical thermal insulation cotton, and the cylindrical thermal insulation cotton corresponds to the protrusion part.

In an embodiment, the metal cup is made of stainless steel or titanium metal.

In an embodiment, the insulation sheet is a mica sheet.

Due to the adoption of the above technical solution, the heating cup component for electric heating incense burner in the present disclosure heats more quickly and evenly, which is beneficial for improving heating efficiency and reducing energy consumption. In addition, it is easy to clean and suitable for battery power supply, thereby improving portability and use range.

Figure 1:
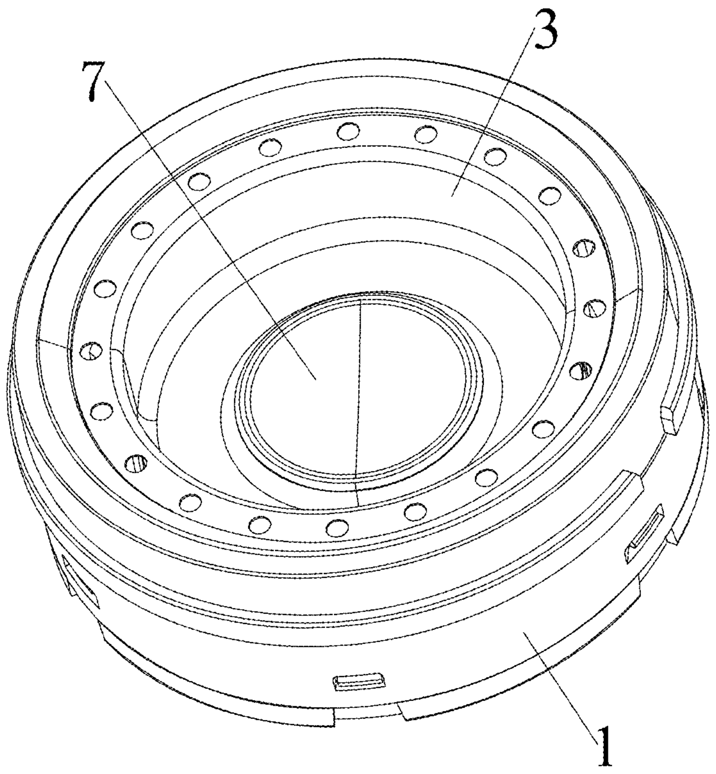
FIG. 1 schematically illustrates a three-dimensional view of the present disclosure.
Figure 2:
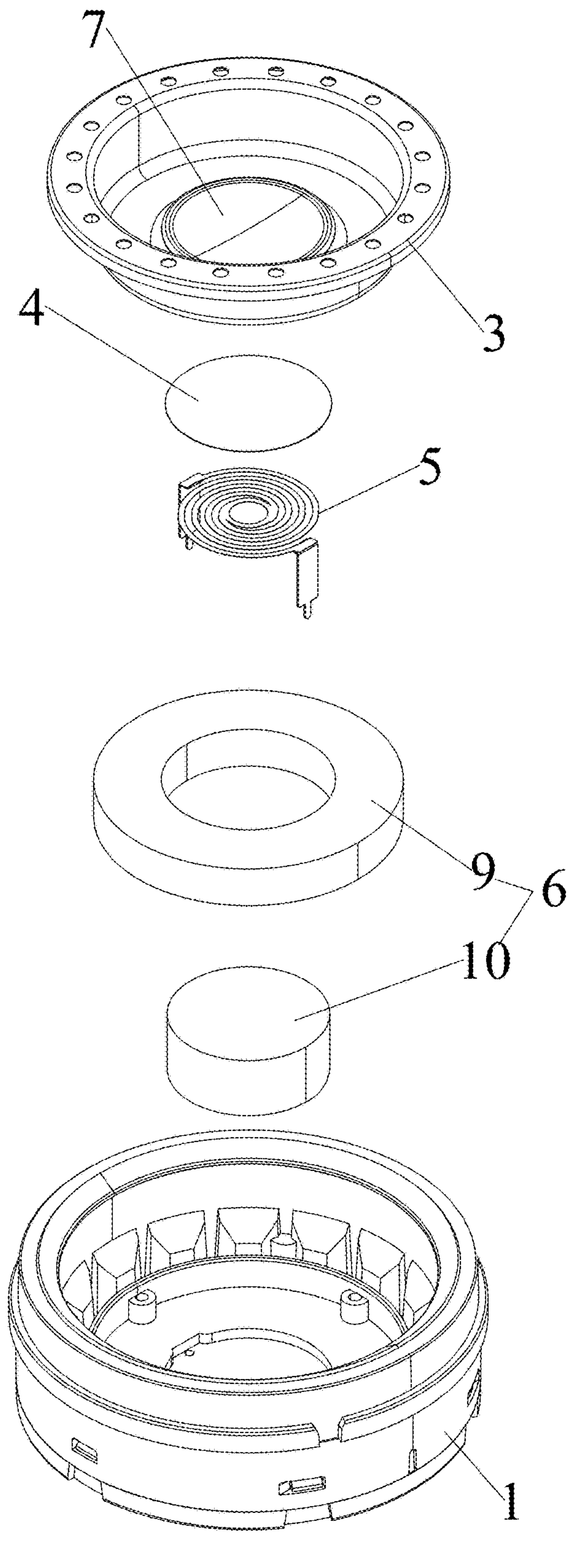
FIG. 2 schematically illustrates an exploded view of the present disclosure.
Figure 3:
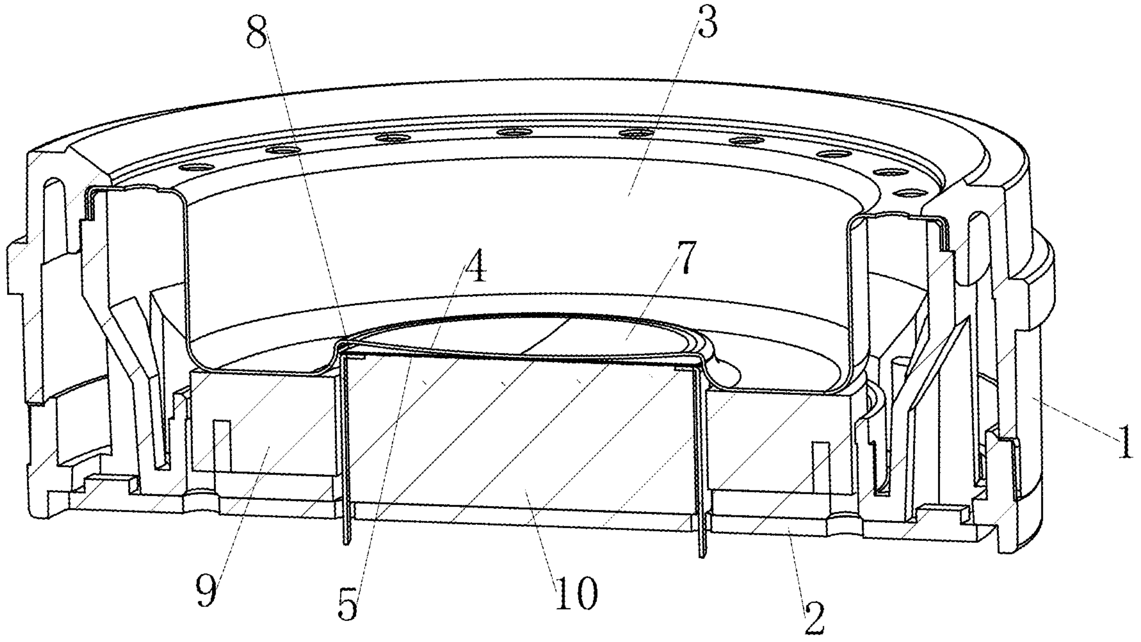
FIG. 3 schematically illustrates a sectional view of the present disclosure.

Numeral reference: 1. Shell; 2. Control board; 3. Metal cup; 4. Insulation sheet; 5. Electric heating wire; 6. Thermal insulation cotton; 7. Protrusion part; 8. Accommodating chamber; 9. Circular thermal insulation cotton; 10. Cylindrical thermal insulation cotton.

DESCRIPTION OF EMBODIMENTS

The following provides a detailed explanation of the embodiments of the present disclosure, but the present disclosure may be implemented in various different ways limited and covered by the claims.

As an aspect of the present disclosure, a heating cup component for an electric heating incense burner is provided, including: a shell 1, a control board 2, a metal cup 3, an insulation sheet 4, an electric heating wire 5, and a thermal insulation cotton 6. The metal cup 3 is provided in the shell 1, the electric heating wire 5 is provided below the metal cup 3, the insulation sheet 4 is provided on an upper surface of the electric heating wire 5, the control board 2 is provided at a bottom of the shell 1, and the thermal insulation cotton 6 is provided between the metal cup 3 and the control board 2.

In an implementation, a bottom of the metal cup 3 has an upward protrusion part 7, and the electric heating wire 5 is located in an accommodating chamber 8 formed by the protrusion part 7. In an implementation, the thermal insulation cotton 6 includes a circular thermal insulation cotton 9 and a cylindrical thermal insulation cotton 10, the circular thermal insulation cotton 9 is sleeved on an outside of the cylindrical thermal insulation cotton 10, the electric heating wire 5 is provided on the cylindrical thermal insulation cotton 10, and the cylindrical thermal insulation cotton 10 corresponds to the protrusion part 7. In this way, the circular thermal insulation cotton 9 and the cylindrical thermal insulation cotton 10 are used to fill and insulate the protrusion part 7 and its lower annular area. At the same time, a conductive sheet or pin of the electric heating wire 5 can be extended downwards from a gap between the circular thermal insulation cotton 9 and the cylindrical thermal insulation cotton 10 to connect with the control board 2 below. A concave surface of the protrusion part 7 is designed to temporarily deposit the oil that precipitates during an initial heating of the incense. When a temperature of the concave surface reaches a combustion temperature, the oil will be completely burned, which can improve a utilization rate of the incense.

In an implementation, the metal cup 3 is made of stainless steel or titanium metal. In an implementation, the insulation sheet 4 is a mica sheet.

In the above technical solution, the present disclosure the electric heating wire 5 is placed on a bottom of an outer side of the metal cup 3, which is configured to place the incense, thereby reducing residue adhesion. The metal cup 3 is easy to clean and maintain, and does not require a incense dish. In addition, the electric heating wire 5 makes the present disclosure more suitable for battery power supply, improves portability and use range. The electric heating wire 5 is provided in the accommodating chamber 8 formed by the protrusion part 7, a thermal convection and a low thermal conductivity of titanium alloy and stainless steel are used to make the protrusion part 7 to be a high-temperature combustion zone with low heat capacity, thereby accelerating heating speed and reducing energy consumption.

Due to the adoption of the above technical solution, the heating cup component for electric heating incense burner in the present disclosure heats more quickly and evenly, which is beneficial for improving heating efficiency and reducing energy consumption. In addition, it is easy to clean and suitable for battery power supply, thereby improving portability and use range.

The above is only a preferred embodiment of the present disclosure and is not intended to limit it. For those skilled in the art, the present disclosure may have various modifications and variations. Any modifications, equivalent replacements, improvements, etc. made within the spirit and principles of the present disclosure shall be included within the protection scope of the present disclosure.

What is claimed is:

1. A heating cup component for an electric heating incense burner, comprising:

a shell, a control board, a metal cup, an insulation sheet, an electric heating wire, and a fibrous insulation material;

wherein the metal cup is provided in the shell, the electric heating wire is provided below the metal cup, the insulation sheet is provided on an upper surface of the electric heating wire, the control board is provided at a bottom of the shell, and the fibrous insulation material is provided between the metal cup and the control board;

wherein a bottom of the metal cup comprises an upward protrusion part, and the electric heating wire is located in an accommodating chamber formed by the protrusion part; and wherein the fibrous insulation material comprises a circular fibrous insulation material and a cylindrical fibrous insulation material, the circular fibrous insulation material is sleeved on an outside of the cylindrical fibrous insulation material, the electric heating wire is provided on the cylindrical fibrous insulation material, and the cylindrical fibrous insulation material corresponds to the protrusion part.

2. The heating cup component for an electric heating incense burner according to claim 1, wherein the metal cup is made of stainless steel or titanium metal.

3. The heating cup component for an electric heating incense burner according to claim 1, wherein the insulation sheet is a mica sheet.

* * * * *